United States Patent [19]

Hultin et al.

[11] Patent Number: 6,136,959
[45] Date of Patent: Oct. 24, 2000

[54] HIGH EFFICIENCY ALKALINE PROTEIN EXTRACTION

[75] Inventors: Herbert O. Hultin, Rockport; Stephen D. Kelleher, Wakefield, both of Mass.

[73] Assignee: University of Massachusetts, Boston, Mass.

[21] Appl. No.: 09/102,709

[22] Filed: Jun. 22, 1998

[51] Int. Cl.[7] .............................. C07K 3/00; C07K 15/00
[52] U.S. Cl. .................... 530/412; 530/418; 530/422; 530/427; 530/827; 426/656; 426/657
[58] Field of Search ..................................... 530/827, 412, 530/418, 422, 427; 426/656, 657

[56] References Cited

U.S. PATENT DOCUMENTS

| | | | |
|---|---|---|---|
| 4,247,573 | 1/1981 | Murray et al. | 426/656 |
| 5,086,166 | 2/1992 | Lawhon et al. | 530/378 |

OTHER PUBLICATIONS

Batista, "Recovery . . . ," Simposium Internacional de Produção de Novas Proteińas e utilização de Recursos Alimentares Inexplorados, Faro, Portugal, Apr. 4–6, 1991.

Montecalvo, J. Jr. et al., "Optimization of Processing Parameters for the Preparation . . . ," Journal of Food Science, vol. 49, p. 172–187, (1984).

Chen et al., "Effects of Acid and Alkaline Reagents on the Color and Gel–forming Ability of Milkfish Kamaboko", Fisheries Science 64:160–163, 1998.

Jelen et al., "Recovery of Meat Protein From Alkaline Extracts of Beef Bones", Journal of Food Science 44:327–331, 1979.

Lopez–Echevarria et al., "Effect of Alkaline Treatment and Sodium Erythorbate on Functional Properties of Surimi Gels Made From Frozen Stored", 1997 IFT Annual Meeting, Book of Abstracts 10–6.

Lopez–Echevarria et al., "Effect of Alkaline Treatment on Physicochemical and Functional Properties of Surimi Gels Made of Miofibrilar Protein From", 1996 IFT Annual Meeting, Book of Abstracts 62–8.

McCurdy et al., "Laboratory and Pilot Scale Recovery of Protein form Mechanically Separated Chicken Residue", Journal of Food Science, 51:742–753, 1986.

Meinke et al., "Autolysis as a Factor in the Production of Protein Isolates from Whole Fish", Journal of Food Science, 38:864–866, 1973.

Meinke et al., "Some Factors Influencing the Production of Protein Isolates From Whole Fish", Journal of Food Science, 37:195–198, 1972.

Murata et al., "Qualitative Improvement of Minced Sardine Meat by a Brief Alkaline Leaching in Vacuo", Nippon Shokuhin Kagaku Kogaku Kaishi, 43:575–581, (1996).

Opiacha et al., "Composition of Dehydrated Protein Extracts from Poultry Bone Residue", Food & Nutrition Journal of Muscle Foods, 5:343–353, 1994.

Shahidi et al., "Base Extraction of Proteins from Seal Meat and Bone Residues", 41st Annual International Congress of Meat Science and Technology, 11:574–575, 1995.

Shahidi et al., "Solubilization and Thermostability of Water Dispersions of Muscle Structural Proteins of Atlantic Herring (*Clupea harengus*)", J. Agric. Food Chem., 42:1440–1446, 1994.

Tannenbaum et al., "Solubilization of Fish Protein Concentrate: 1. An Alkaline Process", Food Technology, 24:96–99, 1970.

Tannenbaum et al., "Solubilization of Fish Protein Concentrate: 2. Utilization of the Alkaline–Process Product", Food Technology, 24:99–101, 1970.

Wimmer et al., "Washed Mechanically Separated Pork as a Surimi–like Meat–product Ingredient", Journal of Food Science, 58:254–258, 1993.

*Primary Examiner*—Marianne M. Cintins
*Assistant Examiner*—C. Delacroix-Muirheid
*Attorney, Agent, or Firm*—Fish & Richardson P.C.

[57] ABSTRACT

A process for isolating edible protein from animal muscle by solubilizing the protein in an alkaline aqueous solution is disclosed.

29 Claims, No Drawings

HIGH EFFICIENCY ALKALINE PROTEIN EXTRACTION

FIELD OF THE INVENTION

This invention relates to a process for isolating edible protein from animal muscle by solubilizing the protein in an alkaline aqueous solution.

BACKGROUND OF THE INVENTION

Surimi or formed fish has been produced in Japan for about a thousand years. Only recently has surimi appeared in North American supermarkets as imitation crab legs, lobster chunks, shrimp, and scallops. North American surimi is typically produced from lean white fish, such as pollack or whiting.

Low value animal muscle (e.g., from fatty pelagic fish or poultry bone residue) is usually undesirable as a source of food for human consumption. After processing, the isolated protein is often characterized by unattractive textures, dark colors, and strong flavors.

SUMMARY OF THE INVENTION

The invention is based on the discovery that if a mixture of animal muscle is significantly diluted with water and treated with a base to achieve a sufficiently low viscosity, and then centrifuged at a sufficient gravitational force, a high yield of membrane lipid-free protein is obtained. The protein solution is then acidified to precipitate the edible protein (including the myofibrillar proteins), which is now free from the membrane lipids, whose oxidation during processing and storage leads to undesirable colors, flavors, or textures. The new method efficiently isolates edible protein from animal muscle, even that of low quality.

In general, the invention features a method for isolating edible protein from animal muscle (e.g., pelagic fish or chicken) by (1) obtaining a mixture of animal muscle and water, where the animal muscle is less than about 15% by weight of the mixture; (2) increasing the pH of the mixture to a level sufficient to solubilize at least 75% of the animal protein in the animal muscle mixture; (3) centrifuging the mixture so that membrane lipids are separated from an aqueous phase, and collecting the aqueous phase; (4) precipitating the protein from the aqueous phase; and (5) collecting the precipitated protein, thereby isolating the edible protein from the animal muscle.

As an alternative to steps (1) and (2) above, the animal muscle can first be obtained, and the mixture formed by adding an aqueous solution to the animal muscle to form the mixture such that the animal muscle is less than about 15% by weight of the mixture, and the aqueous solution is at a pH sufficiently alkaline to solubilize at least 75% of the animal protein in the animal muscle mixture.

In steps (1) or (2), depending on the specific procedure used, the animal muscle can be from about 5% to 12% (e.g., 10%) by weight of the mixture. In addition, the pH of the mixture or aqueous solution added can be above about 10.5. Where the pH of the mixture or aqueous solution needs to be increased, a polyphosphate is preferably added. Preferably, greater than 80, 85, or 90% or higher of the protein is solubilized.

In step (3), the mixture can be centrifuged at greater than 5000×g. Preferably, the neutral lipids are also separated during the centrifugation in step (3). Other methods besides centrifugation can be used to separate the membrane lipids and the aqueous phase.

In step (4), the protein in the aqueous phase can be precipitated by decreasing the pH of the aqueous phase. For example, the pH of the aqueous phase can be decreased to less than about 5.5. In some embodiments, the pH of the aqueous phase is decreased to less than about 4.0 (e.g., 2.5 to 3.5, especially 3.0) and then increased to more than about 5.0. The pH of the aqueous phase can be decreased by adding hydrochloric acid to the aqueous phase. The salt concentration can be optionally adjusted to aid precipitation, and a cryoprotectant optionally added to the precipitated protein.

In step (5), the total precipitated protein can be collected by centrifugation. Preferably, the collected precipitated protein provides a yield of at least 70% (e.g., 80%, 90%, or even higher) of the total animal muscle protein.

Unless otherwise defined, all technical and scientific terms used herein have the same meaning as commonly understood by one of ordinary skill in the art to which this invention belongs. Although suitable methods and materials for the practice or testing of the present invention are described below, other methods and materials similar or equivalent to those described herein, which are well known in the art, can also be used. All publications, patent applications, patents, and other references mentioned herein are incorporated by reference in their entirety. In case of conflict, the present specification, including definitions, will control. In addition, the materials, methods, and examples are illustrative only and not intended to be limiting.

The invention has several advantages. The methods of the invention remove essentially all of the membrane lipids, thereby stabilizing the edible protein against oxidation. This renders the process especially useful with fatty muscle tissues as a feed composition, which are typical of low cost raw materials, such as would be found in the fatty pelagic fish species or mechanically deboned poultry meat.

The process of this invention also provides for increased yield of protein from animal muscle. Greater than about 70% of protein can be typically obtained from muscle tissue using the methods of the invention. In some cases, protein yields of greater than 90% can be achieved. Besides the obvious commercial value of having better yields, the improved yield results in less protein in the waste water during industrial processing, so that environmental pollution is decreased.

The methods of this invention do not require fresh or lean animal muscle as a starting material. Any spoilage (off smells or colors) due to oxidized lipids can be removed using the methods of the invention. In addition, animal parts containing other fatty tissues such as skin can be used, since the offending lipids will be removed. In the case of fish processing, the methods of the invention eliminate the need to fillet the fish prior to protein isolation, thereby reducing the cost of processing. Similarly, by removing the lipids, the methods of the present invention reduce the amount of fat-soluble toxins (e.g., polychlorinated biphenyls or PCBs) in the food product.

Similar advantages are obtained in a similar edible protein product made using the low pH methods described in pending U.S. patent application Ser. No. 08/797,929 filed on Feb. 12, 1997.

Other features and advantages of the invention will be apparent from the following detailed description, and from the claims.

DETAILED DESCRIPTION

The invention relates to a new method of isolating edible protein from animal muscle. The resulting edible protein is relatively free from membrane lipids, is capable of forming a gel, and can be processed into human foods. For example, the methods of the invention can be used to produce surimi from fatty pelagic fish as well as leaner white fish.

I. Isolating Lipid-Free Edible Protein

In general, the invention features a method for isolating edible protein from animal muscle (e.g., pelagic fish or mechanically deboned chicken muscle) by first obtaining a mixture containing animal muscle and water, the animal muscle being less than about 15% (e.g., 5% to 12%, or preferably 10%) by weight of the mixture. Any aqueous solvent, e.g., water, can be used. The muscle is substantially diluted in water such that the solubilized protein suspension/ solution produced in successive steps of the method is of a low enough viscosity so that the lipids can be removed by centrifugation. The viscosity of the protein suspension/ solution is preferably about 75 mPa·s or less, more preferably about 35 mPa·s or less. Viscosity is measured, for example, with a Brookfield Model LVF viscometer (Brookfield Engineering, Stoughton, Mass.) using a #3 or #4 spindle at 60 rpm. The manufacturer's supplied conversion chart is then used to calculate viscosity. The animal muscle can be mechanically ground or homogenized or chopped by hand.

The pH of the mixture is then increased, for example, to greater than about 10.0 (e.g., about 10.0 to 11.5, or about 10.5) so that at least 75%, e.g., 80, 85 or at least 90%, of the animal protein is solubilized.

Alternatively, an aqueous solution having a pH of greater than about 10.0 (e.g., about 10.0 to 11.5, or about 10.5) can be added to animal muscle so that at least 70%, e.g., 80, 85 or at least 90% or more, of the animal protein becomes solubilized.

Protein denaturation and protein hydrolysis is a function of temperature and time in solution, with increasing temperature and time in solution promoting protein denaturation or hydrolysis. Thus, it is desirable to reduce the temperature and the time the protein is in solution. Preferably, the methods of the invention are conducted at about 0° C. to 10° C. (e.g., 0° C., 1° C., 4° C., or 6° C.). The aqueous composition also may contain components such as preservatives which protect proteins from degradation. The ionic strength of the solution can be adjusted to avoid protein precipitation.

The mixture is then centrifuged (preferably at from about 5000×g to 10,000×g, or higher) so that the charged membrane lipids are separated from an aqueous phase, which is collected by, for example, decanting the aqueous phase. Several layers will have formed after centrifugation. At the bottom, the charged membrane lipids and any remaining residue is pelleted. Preferably, the percentage sediment weight is less than 20%, more preferably less than 10%, because a higher sediment percentage indicates that some of the desirable protein has been removed with the undesirable lipids. Percentage sediment weight is defined as the weight of pellet after centrifugation divided by the total homogenate weight. Above the pellet is an aqueous layer containing the solubilized protein. At the top, the neutral lipids (fats and oils), if any, float above the aqueous layer. The neutral lipids can be removed with a pipette before decanting the aqueous phase. Intervening layers can also be present depending on the source of muscle. For example, a gel of entrapped water containing solubilized protein can form between the aqueous layer and the pellet. This gel can be kept with the aqueous layer to increase protein yield. Of course, in industrial applications, the aqueous phase (and other phases, if desired) can be removed during centrifugation using a continuous-flow centrifuge or other industrial scale machinery. Other methods besides centrifugation can be used to separate the lipids from the aqueous phase.

The pH of the aqueous phase is then decreased so that the solubilized proteins precipitate. The yield is preferably at least 70%, more preferably at least 90%. The yield is defined as the precipitated protein mass divided by the total muscle protein mass. In one embodiment, the pH is decreased to about 5.5 or less to precipitate and collect the protein by, for example, centrifugation. In another embodiment, the pH of the aqueous phase is decreased to less than about 4.0 (e.g., about 2.5 to 3.5, or about 3.0) and then increased to more than about 5.0 to precipitate the protein. This further dip in pH may facilitate precipitation of sarcoplasmic proteins at the higher pH. Cryoprotectants (e.g., disaccharides) can be added to the precipitated protein to preserve and protect the product during freezing and storage.

Any acid that does not undesirably contaminate the final product can be used to lower the pH of the centrifuged mixture. For example, organic acids (e.g., malic acid, or tartaric acid) or mineral acids (e.g., hydrochloric acid or sulfuric acid) are suitable. Citric acid which has favorable $pK_a$ values can provide buffering capacity at pH 3 and pH 5.5. Acids that have significant volatility and impart undesirable odors, such as acetic acid or butyric acid, are undesirable.

Likewise, any of several bases can be used to raise the pH. A polyphosphate is preferred since it also functions as an antioxidant and improves the functional properties of the muscle proteins.

Instead of reducing the pH of the solution, protein precipitation can be attained by adding polymers such as polysaccharides, charged polymers, marine hydrocolloids including alginates or carrageenan or the like, either alone or in combination with centrifugation. The salt concentration of the aqueous phase can also be adjusted to facilitate precipitation.

II. Use of Lipid-Free Edible Protein

The new methods can be used to process for human consumption materials that are not presently used as human foods because of their instability and unfavorable sensory qualities. Small pelagic species of fish such as herring, mackerel, menhaden, capelin, anchovies, or sardines are either underutilized or used for nonhuman uses. Approximately one half the fish presently caught in the world are not used for human food. A process that produces an acceptable stable protein concentrate for human consumption opens the use of this material for human consumption.

III. Sources of Animal Muscle

The process of this invention can be used to process flesh that is recovered from fish after the fillets have been removed. This material is typically not used for human food. Similarly, there is very little usage of the skeletons of chickens after parts are removed for retail sale. The methods of the present invention can process such chicken and fish parts to produce edible protein suitable for human consumption. Other underutilized muscle sources useful in the methods of the invention include Antarctic krill, which is available in large quantities but is difficult to convert to human food because of its small size.

Representative suitable starting sources of animal muscle for the processes of this invention include fish fillets, deheaded and gutted fish, crustacea (e.g., krill), molluscs (e.g., squid), chicken, beef, or lamb.

EXAMPLES

The invention will be further described in the following examples, which do not limit the scope of the invention defined by the claims.

Example 1
Titrating pH for Optimal Protein Solubilization

Preparation of fish. Excellent quality Atlantic cod was obtained from local fish processors. Cod muscle was well trimmed, ground to ⅛-inch pieces, mixed with nine parts cold (6° C.) deionized, distilled water for each part muscle, and homogenized in a Polytron PCU 1 machine (Brinkman Instruments, Westbury, N.Y.) at a speed of 76 for 1 minute.

Alkaline solubilization. The pH of the cod homogenate was 6.85. One molar NaOH was added to the homogenates until it reached specific alkaline pH levels in the range of 9.04 to 11.50. The viscosities of the solutions at 4–6° C. at the specific pH values were measured with a Brookfield Model LVF viscometer (Brookfield Engineering, Stoughton, Mass.) using a #3 or #4 spindle at 60 rpm. The manufacturer's supplied conversion chart was used to calculate viscosity. The mixture was then centrifuged at 9,300 rpm in a No. 35 rotor (10,000×g) for 60 minutes using a L5-65B ultracentrifuge, forming a top layer of emulsified oil, a middle aqueous layer containing the solubilized protein, and a membrane pellet. The aqueous layer was collected by removing the oil with a pipette and then decanting the aqueous solution. The viscosity and solubility results are shown in Table 1.

TABLE 1

| pH | viscosity (mPa · s) | % protein solubility | % sediment weight |
|---|---|---|---|
| 9.04 | 373.5 | 33.37 | 31.18 |
| 9.50 | 409.0 | 36.85 | 40.42 |
| 10.00 | 638.5 | 78.82 | 28.22 |
| 10.49 | 59.5 | 88.90 | 15.08 |
| 10.99 | 57.4 | 99.56 | 13.52 |
| 11.50 | 29.5 | >99.9 | 4.95 |
| 6.85 | 222.5 | — | — |

Protein mass was determined by using the Biuret reaction as described in Torten et al., *J. Food Sci.* 168:168–174 (1963). The percentage protein solubility is defined as protein mass in aqueous layer divided by protein mass in original homogenate. The percentage sediment weight is the weight of sediment after centrifugation divided by the total homogenate weight. High sediment weight values are indicative of protein removed with the membrane lipids. The bottom row in Table 1 represents the homogenate prior to adjustment with 1 M NaOH.

Table I indicates that greater than 70% protein solubility occurs at pH values above 10.0, viscosity drops below 75 mPa·s at pH values between 10.0 and 10.5 and above, and percentage sediment weight drops below 15% at about pH 10.5 or above. The data in Table 1 show that efficient protein solubility (>70%) occurs at pH values above about 10.5. As the viscosity drops below 75 mPa·s when the pH is above about 10.5, the percent protein solubility increases to above 75%. Similarly, percentage sediment weight decreases to below 15% when the pH rises above 10.5. If the viscosity was too high, the protein co-sedimented with the membrane and was removed. A viscosity of 75 mPa·s or less was typically needed to remove the membrane lipids by centrifugation, without removing a substantial portion of the protein along with them. The sample at pH 10 was highly viscous with good protein solubility. This sample, however, would have been difficult to work with in an industrial setting. Sediment weight percentages of about 15% or lower was considered acceptable. Thus, although a pH of about 10.0 could be used, higher pH values approaching and above 10.5 were of greater commercial interest.

Example 2
Production of Cod and Mackerel Surimi

Cod was prepared as described in Example 1 above. Atlantic mackerel was also obtained from local fish processors and processed as described in Example 1. The mackerel was of Stage II quality as assessed using the method described in Kelleher et al., *J. Food. Sci.* 57:1103–1108 and 1119 (1992). The mixtures were adjusted to pH 10.5 to solubilize the protein. The mixtures were then spun, and the aqueous layer collected as described in Example 1.

One molar HCl was added to the aqueous protein solution until it reached pH 5.5. The precipitated protein was collected by centrifuging at 15,000 rpm (34,600×g) in a No. 19 rotor for 20 minutes in a Beckman L5-65B ultracentrifuge. The supernatant was decanted. A cryoprotectant solution containing 4% sucrose, 4% sorbitol, and 1.2% sodium tripolyphosphate was added to the protein pellet. The mixture was formed into surimi by chopping for 30 seconds using an Oskar model chopper (Sunbeam-Oster, Hattiesburg, Mass.) in a refrigerated, walk-in cooler. The surimi was packed into polyethylene Whirl-pak® bags and frozen at −40° C. for at least 12 hours.

The frozen surimi was tempered in a walk-in cooler (4° C.) for 30 minutes prior to chopping for 2 minutes in the Oskar chopper. NaCl was added to 3% (w/w) of surimi during chopping. The chopped paste was stuffed into stainless steel tubes (19 mm diameter×175 mm) and cooked at 90° C. for 20 minutes. The cooked surimi was set in ice for 20 minutes prior to being discharged from the tubes and held for 24 hours at 6° C. Physical properties of the cooked food product are shown in Table 2. Gel strength and displacement values were determined using a 5 mm stainless steel probe attached to an Instron Model 1000 Universal Materials Testing Instrument (Instron Corp., Canton, Mass.) equipped with a 5 kg load cell and a crosshead speed of 100 mm/min. The values were recorded and calculated as described in Lanier, "Measurement of Surimi Composition and Functional Properties," In: *Surimi Technology* (Lanier et al., eds.), pp 123–163, Marcel Dekker, Inc., New York (1992).

TABLE 2

| Muscle Source | Strain | Stress (kPa) |
|---|---|---|
| Cod[1] | 2.21 ± 0.10 | 128.13 ± 7.33 |
| Mackerel[2] | 1.95 ± 0.08 | 91.2 ± 0.00 |

For cod, the values represent the average and standard deviation of three cooked tubes from one gel sample. For mackerel, the values represent the average and standard deviation of two cooked tubes from one gel sample.

All gels were of good quality. In general, values of strain (elastic component) greater than 1.9 to 2.0 are rated as grade A gels. Stress (hardness component) values found in all gels were excellent, with most commercially available gels being at least about 30–35 kPa.

Example 3
Surimi Production Using Very Low pH for Protein Precipitation

Mackerel muscle is prepared, and the protein solubilized at pH 10.5 as described in Example 1 above. The aqueous phase is collected after centrifugation, and hydrochloric acid added until the solution/mixture reaches a pH of 3.0. A significant fraction of the protein is still solubilized. Sodium pyrophosphate is then added to the solution/mixture until the pH reaches 5.5, at which point greater than 95% of the solubilized protein precipitates. The isolated protein is then processed into surimi as described in Example 2 above.

Other embodiments are within the following claims.

What is claimed is:

1. A method for isolating edible protein from animal muscle, the method comprising:
    (a) obtaining a mixture comprising animal muscle and water, wherein the animal muscle comprises less than about 15% by weight of the mixture;
    (b) increasing the pH of the mixture to a level sufficient to solubilize at least 75% of the animal protein in the animal muscle mixture;
    (c) centrifuging the mixture, after at least 75% of the animal protein is solubilized, at about 5,000×g or higher so that membrane lipids are separated from an aqueous phase, and collecting the aqueous phase;
    (d) precipitating the protein from the aqueous phase; and
    (e) collecting the precipitated protein, thereby isolating the edible protein from the animal muscle, wherein the collected precipitated protein provides a yield of at least 70% of the total animal muscle protein.

2. The method of claim 1, wherein the protein in the aqueous phase is precipitated by decreasing the pH of the aqueous phase.

3. The method of claim 2, wherein the pH of the aqueous phase is decreased to less than about 5.5.

4. The method of claim 2, wherein the pH of the aqueous phase is decreased to less than about 4.0 and then increased to more than about 5.0.

5. The method of claim 2, wherein the pH of the aqueous phase is decreased to about 2.5 to 3.5 and then increased to more than about 5.0.

6. The method of claim 2, wherein the pH of the aqueous phase is decreased to about 3.0 and then increased to more than about 5.0.

7. The method of claim 2, wherein the pH of the aqueous phase is decreased by adding hydrochloric acid to the aqueous phase.

8. The method of claim 1, wherein the total precipitated protein is collected by centrifugation.

9. The method of claim 1, wherein the animal muscle comprises from about 5% to 12% by weight of the mixture.

10. The method of claim 1, wherein the animal muscle comprises about 10% by weight of the mixture.

11. The method of claim 1, wherein the pH of the mixture is increased to above about 10.0.

12. The method of claim 1, wherein the pH of the mixture is increased to greater than about 10.5.

13. The method of claim 1, wherein the pH of the mixture is increased by adding a polyphosphate to the mixture.

14. The method of claim 1, wherein greater than about 90% of the animal muscle protein is solubilized.

15. The method of claim 1, wherein the centrifugation is sufficient to separate the neutral lipids from the aqueous phase.

16. The method of claim 1, wherein the salt concentration of the aqueous phase is adjusted to facilitate protein precipitation.

17. The method of claim 1, further comprising adding a cryoprotectant to the precipitated protein.

18. The method of claim 1, wherein the animal muscle is pelagic fish muscle.

19. The method of claim 1, wherein the animal muscle is chicken muscle.

20. The method of claim 1, wherein the pH of the aqueous solution is above about 10.5.

21. The method of claim 1, wherein steps (a)–(c) are performed at a temperature sufficient to substantially inhibit muscle protein denaturation and hydrolysis.

22. The method of claim 21, wherein the temperature is about 0° C. to 10° C.

23. The method of claim 1, wherein the animal muscle is fish muscle.

24. A method for isolating edible protein from animal muscle, the method comprising:
    (a) obtaining animal muscle;
    (b) adding an aqueous solution to the animal muscle to form a mixture such that the animal muscle comprises less than about 15% by weight of the mixture, wherein the pH of the aqueous solution is sufficiently alkaline to solubilize at least 75% of the animal protein in the animal muscle mixture;
    (c) centrifuging the mixture, after at least 75% of the animal muscle protein is solubilized, at about 5000×g or higher so that membrane lipids are separated from an aqueous phase, and collecting the aqueous phase;
    (d) precipitating the protein from the aqueous phase; and
    (e) collecting the precipitated protein, thereby isolating the edible protein from the animal muscle, wherein the collected precipitated protein provides a yield of at least 70% of the total animal muscle protein.

25. The method of claim 24, wherein the protein in the aqueous phase is precipitated by decreasing the pH of the aqueous phase.

26. The method of claim 25, wherein the pH of the aqueous phase is decreased to less than about 5.5.

27. The method of claim 25, wherein the pH of the aqueous phase is decreased to less than about 4.0 and then increased to more than about 5.0.

28. The method of claim 24, wherein steps (a)–(c) are performed at a temperature sufficient to substantially inhibit muscle protein denaturation and hydrolysis.

29. The method of claim 28, wherein the temperature is about 0° C. to 10° C.

* * * * *